(12) United States Patent
Benichou et al.

(10) Patent No.: US 9,241,792 B2
(45) Date of Patent: Jan. 26, 2016

(54) TWO-STEP HEART VALVE IMPLANTATION

(75) Inventors: Netanel Benichou, Nir Etzion D.N. Hof-Carmel (IL); Son V. Nguyen, Irvine, CA (US); Benjamin Spenser, Bat-Shlomo (IL)

(73) Assignee: Edwards Lifesciences Corporation, Irvine, CA (US)

(*) Notice: Subject to any disclaimer, the term of this patent is extended or adjusted under 35 U.S.C. 154(b) by 1310 days.

(21) Appl. No.: 12/392,995

(22) Filed: Feb. 25, 2009

(65) Prior Publication Data

US 2009/0281609 A1 Nov. 12, 2009

Related U.S. Application Data

(60) Provisional application No. 61/032,822, filed on Feb. 29, 2008.

(51) Int. Cl.
*A61F 2/24* (2006.01)

(52) U.S. Cl.
CPC ............ *A61F 2/2418* (2013.01); *A61F 2/2433* (2013.01); *A61F 2220/0008* (2013.01); *A61F 2220/0016* (2013.01); *A61F 2230/0054* (2013.01); *A61F 2250/0059* (2013.01); *A61F 2250/0063* (2013.01)

(58) Field of Classification Search
CPC ... A61F 2/2427; A61F 2/2433; A61F 2/2436; A61F 2/2439; A61F 2/2469; Y10S 623/90; Y10S 623/902; Y10S 623/904
USPC .................... 623/1.11, 1.24, 1.26, 2.11–2.19, 623/2.36–2.38, 900, 902, 904
See application file for complete search history.

(56) References Cited

U.S. PATENT DOCUMENTS 3,476,101 A 9/1965 Fogarty et al.
3,409,013 A 11/1968 Berry
(Continued)

FOREIGN PATENT DOCUMENTS

DE 2246526 3/1973
DE 19532846 3/1997
(Continued)

OTHER PUBLICATIONS

Andersen, et al., "Transluminal implantation of artificial heart valves. Description of a new expandable aortic valve and initial results with implantation by catheter technique in closed chest pigs." European Heart Journal (1992), 13, 704-708.
(Continued)

*Primary Examiner* — Diane Yabut
(74) *Attorney, Agent, or Firm* — David L. Hauser; Pui Tong Ho

(57) ABSTRACT

A two-part implantable heart valve and procedure are disclosed that allow expansion and positioning of a first part of the implantable heart valve having a temporary or transient valvular structure. A second part of the implantable heart valve is deployed within the first part and attaches thereto. The valvular structure of the second part then acts to function as the heart valve replacement. A tool or system is provided for determining an adequate percutaneous heart valve size for a given stenotic valve. A balloon can be inflated inside the stenotic valve to a desired pressure. When this pressure is reached an angiographic image is taken and the balloon diameter is measured at a waist area created by contact between the balloon and the stenotic valve. The diameter represents the minimum percutaneous heart valve diameter to be implanted.

22 Claims, 5 Drawing Sheets

(56) References Cited

U.S. PATENT DOCUMENTS

| | | |
|---|---|---|
| 3,548,417 A | 12/1970 | Kisher |
| 3,570,014 A | 3/1971 | Hancock |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Sammuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely |
| 5,554,185 A | 9/1996 | Block et al. |
| 5,571,175 A | 11/1996 | Vanney et al. |
| 5,591,185 A | 1/1997 | Kilmer et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler |
| 5,855,602 A | 1/1999 | Angell |
| 5,925,063 A | 7/1999 | Khosravi |
| 5,935,163 A | 8/1999 | Gabbay |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,174,329 B1 | 1/2001 | Callol et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian |
| 6,302,906 B1 | 10/2001 | Goicoechea et al. |
| 6,350,277 B1 | 2/2002 | Kocur |
| 6,350,282 B1 | 2/2002 | Eberhardt |
| 6,371,983 B1 | 4/2002 | Lane |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle |
| 6,482,228 B1 | 11/2002 | Norred |
| 6,488,704 B1 | 12/2002 | Connelly et al. |
| 6,569,196 B1 | 5/2003 | Vesely et al. |
| 6,605,112 B1 | 8/2003 | Moll |
| 6,730,118 B2 | 5/2004 | Spenser et al. |
| 6,733,525 B2 | 5/2004 | Yang et al. |
| 6,830,584 B1 | 12/2004 | Seguin |
| 6,893,460 B2 | 5/2005 | Spenser et al. |
| 6,908,481 B2 * | 6/2005 | Cribier ........................ 623/2.11 |
| 7,018,406 B2 | 3/2006 | Seguin et al. |
| 7,198,646 B2 | 4/2007 | Figulla et al. |
| 7,261,732 B2 | 8/2007 | Justino |
| 7,276,078 B2 | 10/2007 | Spenser et al. |
| 7,276,084 B2 | 10/2007 | Yang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,470,285 B2 | 12/2008 | Nugent et al. |
| 7,585,321 B2 | 9/2009 | Cribier |
| 7,758,632 B2 | 7/2010 | Hojeibane et al. |
| 2001/0021872 A1 | 9/2001 | Bailey et al. |
| 2002/0032481 A1 | 3/2002 | Gabbay |
| 2002/0173842 A1 | 11/2002 | Buchanan |
| 2002/0188348 A1 | 12/2002 | DiMatteo et al. |
| 2003/0050694 A1 | 3/2003 | Yang et al. |
| 2003/0100939 A1 | 5/2003 | Yodfat et al. |
| 2003/0199963 A1 | 10/2003 | Tower et al. |
| 2003/0212454 A1 | 11/2003 | Scott et al. |
| 2004/0019374 A1 | 1/2004 | Hojeibane et al. |
| 2004/0039436 A1 | 2/2004 | Spenser et al. |
| 2004/0049262 A1 | 3/2004 | Obermiller et al. |
| 2004/0122516 A1 | 6/2004 | Fogarty et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0043790 A1 | 2/2005 | Seguin |
| 2005/0137682 A1 * | 6/2005 | Justino ........................ 623/1.24 |
| 2005/0137696 A1 * | 6/2005 | Salahieh et al. ............. 623/2.11 |
| 2005/0234546 A1 | 10/2005 | Nugent et al. |

(56) References Cited

U.S. PATENT DOCUMENTS

| | | | |
|---|---|---|---|
| 2005/0240200 A1* | 10/2005 | Bergheim | 606/108 |
| 2005/0251251 A1 | 11/2005 | Cribier | |
| 2006/0025857 A1 | 2/2006 | Bergheim et al. | |
| 2006/0052802 A1* | 3/2006 | Sterman et al. | 606/148 |
| 2006/0052867 A1* | 3/2006 | Revuelta et al. | 623/2.18 |
| 2006/0149350 A1 | 7/2006 | Patel et al. | |
| 2006/0229719 A1 | 10/2006 | Marquez et al. | |
| 2006/0259137 A1 | 11/2006 | Artof et al. | |
| 2008/0154355 A1 | 6/2008 | Benichou et al. | |
| 2009/0069887 A1* | 3/2009 | Righini et al. | 623/2.11 |

FOREIGN PATENT DOCUMENTS

| | | |
|---|---|---|
| DE | 19546692 | 6/1997 |
| DE | 19857887 | 7/2000 |
| DE | 19907646 | 8/2000 |
| DE | 10049812 | 4/2002 |
| DE | 10049813 | 4/2002 |
| DE | 10049814 | 4/2002 |
| DE | 10049815 | 4/2002 |
| EP | 0103546 | 3/1984 |
| EP | 0144167 | 6/1985 |
| EP | 0597967 | 12/1994 |
| EP | 0592410 | 10/1995 |
| EP | 0850607 | 7/1998 |
| EP | 1057460 | 12/2000 |
| EP | 1088529 | 4/2001 |
| EP | 1570809 | 9/2005 |
| FR | 2788217 | 7/2007 |
| GB | 2056023 | 3/1981 |
| SU | 1271508 | 11/1986 |
| WO | WO 91/17720 | 11/1991 |
| WO | WO 92/17118 | 10/1992 |
| WO | WO 93/001768 | 2/1993 |
| WO | WO 97/24080 | 7/1997 |
| WO | WO 98/29057 | 7/1998 |
| WO | WO 99/33414 | 7/1999 |
| WO | WO 99/40964 | 8/1999 |
| WO | WO 99/47075 | 9/1999 |
| WO | WO 00/18333 | 4/2000 |
| WO | WO 00/41652 | 7/2000 |
| WO | WO 00/44313 | 8/2000 |
| WO | WO 00/47139 | 8/2000 |
| WO | WO 01/35878 | 5/2001 |
| WO | WO 01/49213 | 7/2001 |
| WO | WO 01/54624 | 8/2001 |
| WO | WO 01/54625 | 8/2001 |
| WO | WO 01/62189 | 8/2001 |
| WO | WO 01/64137 | 9/2001 |
| WO | WO 01/76510 | 10/2001 |
| WO | WO 02/22054 | 3/2002 |
| WO | WO 02/36048 | 5/2002 |
| WO | WO 02/41789 | 5/2002 |
| WO | WO 02/43620 | 6/2002 |
| WO | WO 02/47575 | 6/2002 |
| WO | WO 02/49540 | 6/2002 |
| WO | WO 03/003943 | 1/2003 |
| WO | WO 03/047468 | 6/2003 |
| WO | WO 2005/087140 | 9/2005 |
| WO | WO 2006/014233 | 2/2006 |
| WO | WO 2006/034008 | 3/2006 |
| WO | WO 2006/127765 | 11/2006 |
| WO | WO 2007/081820 | 7/2007 |
| WO | WO 2008/005405 | 1/2008 |
| WO | WO 2008/035337 | 3/2008 |
| WO | WO 2008/147964 | 12/2008 |
| WO | WO 2008/150529 | 12/2008 |

OTHER PUBLICATIONS

Andersen, Henning Rud, "History of Percutaneous Aortic Valve Prosthesis," Herz 34 2009 No. 5, Urban & Vogel, pp. 343-346, Skejby University Hospital Department of Cardiology, Aarhus, Denmark.

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Serruys, P.W., et al., "Stenting of Coronary Arteries. Are we the Sorcerer's Apprentice?," European Heart Journal (1989) 10, 774-782, pp. 37-45, Jun. 13, 1989.

Kolata, Gina, "Device That Opens Clogged Arteries Gets a Failing Grade in a New Study," nytimes.com, http://www.nytimes.com/1991/01/03/health/device-that-opens-clogged-arteries-qets-a-faili . . . , Jul. 29, 2009, 2 pages.

Urban, M.D., Philip, "Coronary Artery Stenting," Editions Medecine et Hygiene, Geneve, 1991, pp. 5-47.

Al-Khaja, N., et al., "Eleven Years' Experience with Carpentier-Edwards Biological Valves in Relation to Survival and Complications," European Journal of Cardiothoracic Surgery 3:305-311, Jun. 30, 2009.

Wheatley, M.D., David J., "Valve Prostheses," Rob & Smith's Operative Surgery, Fourth Edition, pp. 415-424, Butterworths 1986.

Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.

Uchida, Barry T., et al., "Modifications of Gianturco Expandable Wire Stents," AJR:150, May 1988, Dec. 3, 1987, pp. 1185-1187.

Selby, M.D., J. Bayne, "Experience with New Retrieval Forceps for Foreign Body Removal in the Vascular, Urinary, and Biliary Systems," Radiology 1990; 176:535-538.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Al Zaibag, Muayed, et al., "Percutaneous Balloon Valvotomy in Tricuspid Stenosis," British Heart Journal, Jan. 1987, vol. 57, No. 1, pp. 51-53.

Lawrence, Jr., M.D., David D., "Percutaneous Endovascular Graft: Experimental Evaluation," Radiology 1897; 163: 357-360.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Rashkind, M.D., William J., "Historical Aspects of Interventional Cardiology: Past, Present, Future," Texas Heart Institute Journal, Interventional Cardiology, pp. 363-367.

Rösch, M.D., Josef, "The Birth, Early Years and Future of Interventional Radiology," J Vasc Interv Radiol 2003; 14:841-853.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Ross, F.R.C.S., D.N., "Aortic Valve Surgery," Guy's Hospital, London, pp. 192-197, approximately 1968.

Rashkind, M.D., William J., "Creationof an Atrial Septal Defect Withoput Thoracotomy," the Journal of the American Medical Association, vol. 196, No. 11, Jun. 13, 1966, pp. 173-174.

Porstmann, W., et al., "Der Verschluβ des Ductus Arteriosus Persistens ohne Thorakotomie," Thoraxchirurgie Vaskuläre Chirurgie, Band 15, Heft 2, Stuttgart, im Apr. 1967, pp. 199-203.

Curriculum Vitae of Robert A. Ersek, M.D., FACS, Jul. 10, 2009, http://www.ersek.com/rae-cv.htm.

* cited by examiner

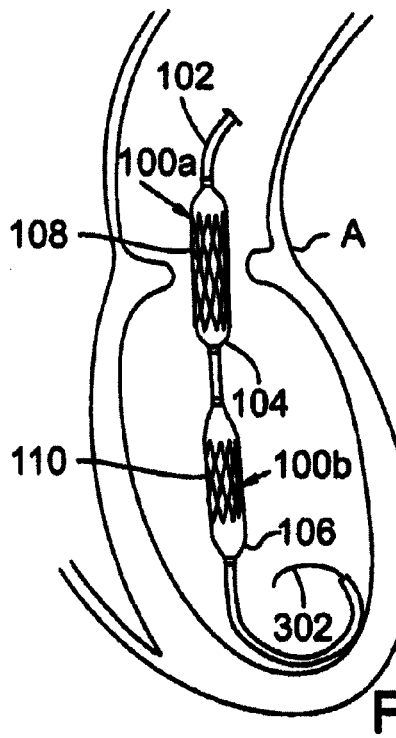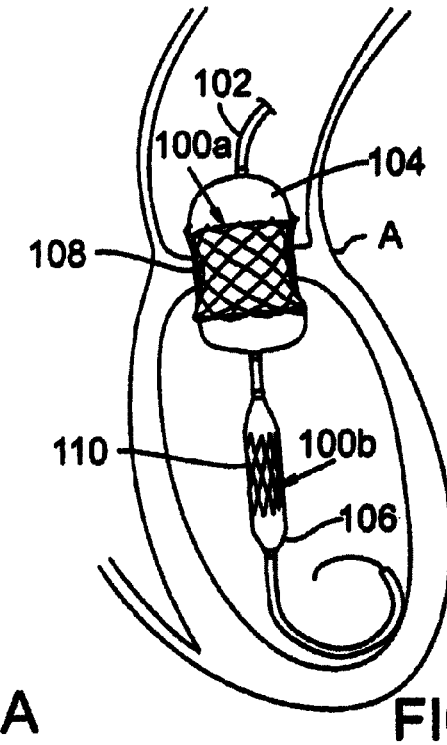
FIG. 3A  FIG. 3B
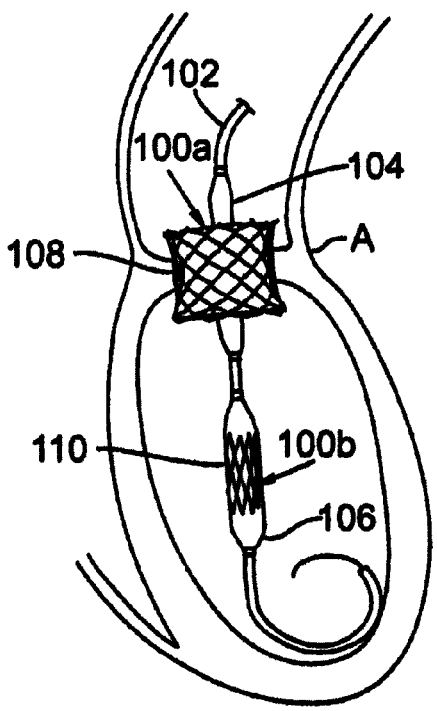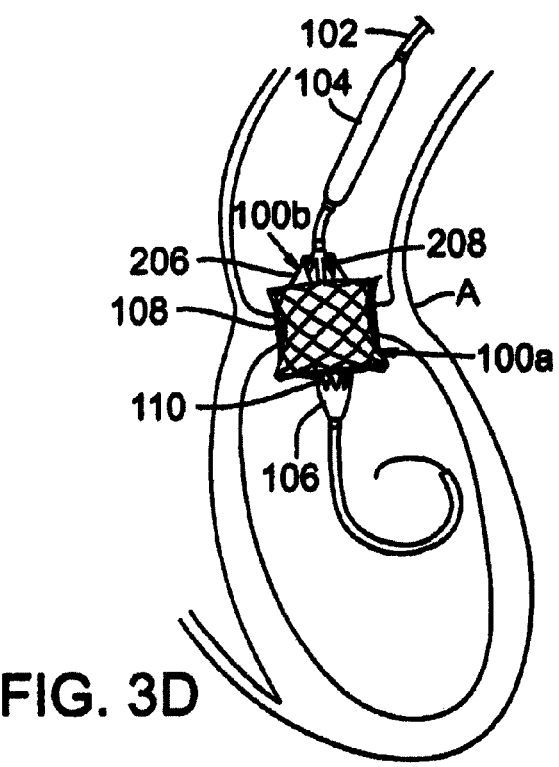
FIG. 3C  FIG. 3D

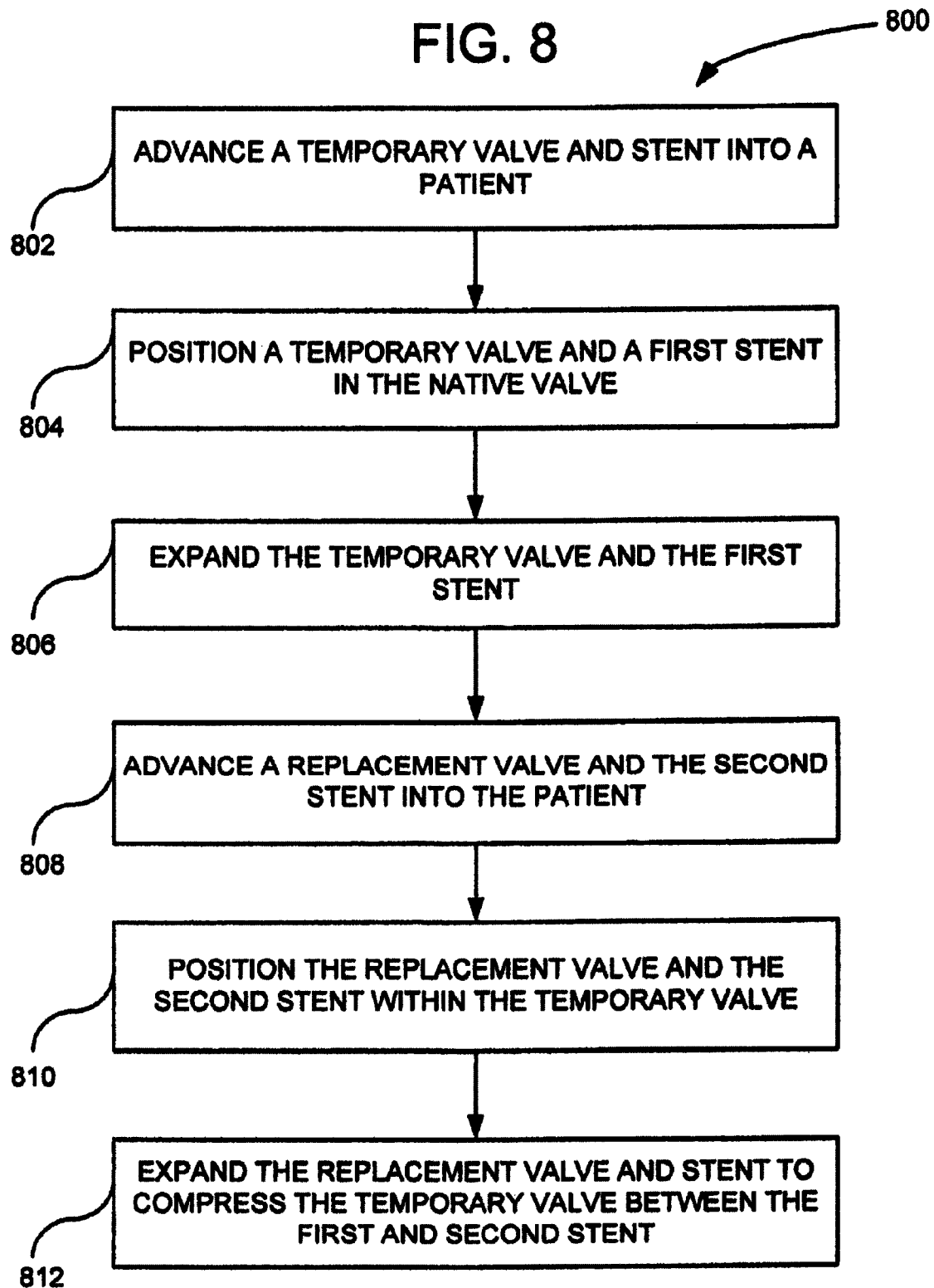

TWO-STEP HEART VALVE IMPLANTATION

CROSS-REFERENCE TO RELATED APPLICATIONS

The present application claims the benefit of U.S. Provisional Application No. 61/032,822, filed Feb. 29, 2008, which is hereby incorporated by reference.

FIELD

The present disclosure concerns an implantable device and, more particularly, to a valve prosthesis for cardiac implantation.

BACKGROUND

A percutaneous heart valve implantation (PHV) has been developed by Edwards Lifesciences PVT Ltd. and is described in U.S. Pat. No. 6,730,118, which is herein incorporated by reference in its entirety. A primary concept behind using a PHV is implantation inside the stenotic region of a calcified native valve without removing the native valve. The PHV stents the stenotic valve open and uses it as an attachment means for the PHV.

A major design parameter of the PHV is the folded or crimped profile. The crimped profile directly influences the ability to insert the PHV into the femoral artery or vein. Accordingly, a smaller profile allows for treatment of a wider population of patients, with enhanced safety.

Generally, the primary attachment mechanism of the PHV to the native valve is friction. This friction is generated by radial contact forces between the stenotic valve and the metallic frame of the PHV. A proper sizing should provide for secure attachment of the PHV to the native valve and provide good sealing to avoid, for example, paravalvular leaks.

Prior PHV implantation methods and apparatus include Schreck in U.S. Pat. No. 6,454,799, entitled, "MINIMALLY-INVASIVE HEART VALVES AND METHODS OF USE", which describes expandable heart valves for minimally invasive valve replacement surgeries. In a first embodiment, an expandable pre-assembled heart valve includes a plastically-expandable annular base having a plurality of upstanding commissure posts. A tubular flexible member including a prosthetic section and a fabric section is provided, with the prosthetic section being connected to the commissure posts and defining leaflets therebetween, and the fabric section being attached to the annular base. In a second embodiment, an expandable heart valve includes an annular tissue-engaging base and a subassembly having an elastic wireform and a plurality of leaflets connected thereto. The annular base and subassembly are separately stored and connected just prior to delivery to the host annulus. The leaflet subassembly is stored in its relaxed configuration to avoid deformation of the leaflets. The expandable heart valves can be implanted using a balloon catheter. The leaflets of the heart valves are secured to the commissure regions of the expandable stents using a clamping arrangement to reduce stress.

Spenser et al. in U.S. patent application No. 20030153974, entitled "IMPLANTABLE PROSTHETIC VALVE", describes a prosthesis device suitable for implantation in body ducts. The device has a support stent that is adapted to be initially crimped in a narrow configuration suitable for catheterization through a body duct to a target location and adapted to be deployed by exerting substantially radial forces from within by means of a deployment device. The support stent includes a plurality of longitudinally rigid support beams of fixed length, and a valve assembly comprising a flexible conduit having an inlet and an outlet made of pliant material attached to the support beams to provide collapsible slack portions of the conduit at the outlet. When flow is allowed to pass through the valve prosthesis device from the inlet to the outlet, the valve assembly is kept in an open position, whereas a reverse flow is prevented due to the collapsible slack portions of the valve assembly that collapse inwardly to block the reverse flow.

Another known technique for implanting a prosthetic valve is a transapical approach where a small incision is made in the chest wall of a patient and the catheter is advanced through the apex (i.e., bottom tip) of the heart. Transapical techniques are disclosed in U.S. Patent Application Publication No. 20070112422, which is hereby incorporated by reference. Like the transvascular approach, the transapical approach includes a balloon catheter having a steering mechanism for delivering a balloon-expandable prosthetic heart valve through an introducer to the aortic annulus. The balloon catheter includes a deflecting segment just proximal to the distal balloon to facilitate positioning of the prosthetic heart valve in the proper orientation within the aortic annulus.

Yet another known technique for implantation of a prosthetic in the aortic valve is through the use of a two-balloon catheter. For example, such a system is shown in U.S. Pat. No. 6,908,481, entitled "VALUE PROSTHESIS FOR IMPLANTATION IN BODY CHANNELS." Typically, two balloons are fixed on a catheter shaft and are separated by a few millimeters. The first balloon carries a frame for scaffolding a stenosed orifice after initial dilatation and the second balloon carries an expandable valve. The first balloon is sufficiently strong to avoid bursting even at very high pressure. The second balloon does not need to be as strong as the first and can, therefore, be thinner, occupying less space and being easier to expand with lower pressure. The time interval between expansion of the first and second balloons must be short because there is a total aortic regurgitation back through the frame towards the left ventricle. Such a regurgitation is a hemodynamic condition that cannot be maintained for more than a few seconds.

In order to decrease the possibility of aortic regurgitation, U.S. Pat. No. 6,425,916, entitled "METHODS AND DEVICES FOR IMPLANTING CARDIAC VALVES" introduces a temporary valve. However, the temporary valve must be removed after the permanent valve is deployed, which requires an additional surgical step and potential complication.

SUMMARY

The present invention provides a two-part implantable heart valve and procedure, which allows expansion and positioning of a first part of the implantable heart valve using a temporary or transient valvular structure. The second part of the implantable heart valve is deployed within the first part. The valvular structure of the second part then acts to function as the heart valve replacement. The second part of the implantable heart valve displaces the temporary valve and compresses the temporary valve between a first frame associated with the first part and second frame associated with the second part to increase friction therebetween and reduce paravalvular leakage. The temporary valve is, therefore, used as a part of the permanent heart valve replacement and need not be removed.

Advantageously, separating the two-part valve and delivering the parts in series reduces the crimped profile of the implantable valve so a wider population can be treated. In addition, the first part can be deployed using a strong pressure inflation of a balloon without the risk of damaging the primary valvular structure associated with the second part, which uses only light pressure inflation. Alternatively, either one or both of the parts can be self expanding.

A tool or system is provided for determining an adequate PHV size for a given stenotic valve. A balloon can be inflated inside the stenotic valve to a desired pressure. When the desired pressure is reached an angiographic image is taken and the balloon diameter is measured in a waist area created by contact between the balloon and the stenotic valve. The diameter represents the minimum PHV diameter to be implanted.

The foregoing and other features and advantages will become more apparent from the following detailed description, which proceeds with reference to the accompanying figures.

BRIEF DESCRIPTION OF THE DRAWINGS

FIGS. 3A-3F illustrate possible steps for implantation of the valve of FIG. 1 with a two-balloon catheter.

FIG. 8 is a flowchart of a method for implanting a heart valve using a two step approach with a temporary valve.

DETAILED DESCRIPTION

The following description is exemplary in nature and is not intended to limit the scope, applicability, or configuration of the invention in any way. Various changes to the described embodiments can be made in the function and arrangement of the elements described herein.

As used herein, the singular forms "a,", "an," and "the" refer to one or more than one, unless the context clearly dictates otherwise.

As used herein, the term "includes" means "comprises." For example, a device that includes or comprises A and B contains A and B but can optionally contain C or other components other than A and B. A device that includes or comprises A or B can contain A or B or A and B, and optionally one or more other components such as C.

Figure 1:
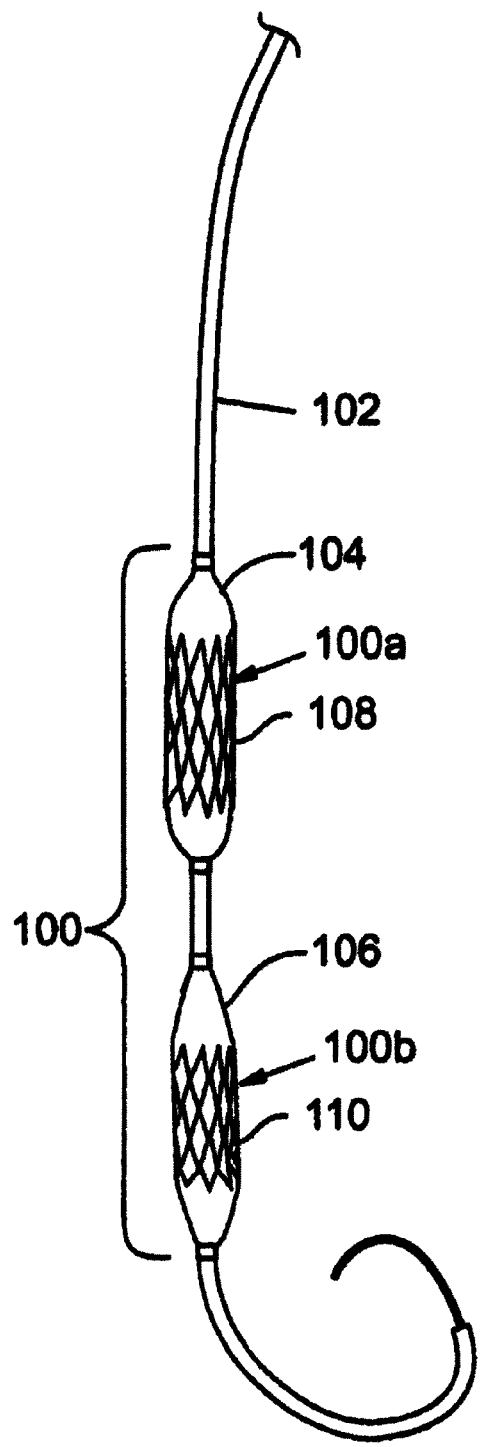
FIG. 1 is a simplified illustration of an embodiment of an implantable valve mounted in two parts on a delivery catheter.

FIG. 1 is a simplified illustration of an implantable valve 100 that can be made in two parts 100a and 100b in accordance with a first embodiment. A catheter 102 can have two-balloons, a proximal balloon 104 and a distal balloon 106 fixed to catheter 102 in close proximity. In one embodiment, the two-balloon catheter 102 can include at least two lumens for successive and separate inflation of each balloon. The embodiments below are generally described with reference to the aortic valve, but each embodiment can be used with other cardiac valves.

Figure 2A:
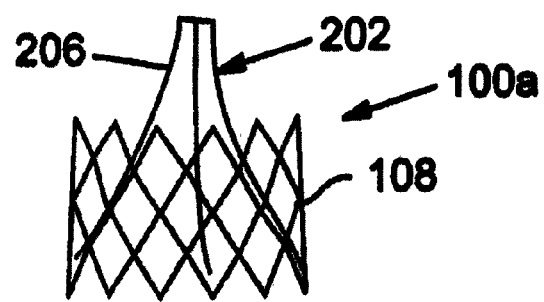
FIGS. 2A and 2B are simplified illustrations of the two parts of the implantable valve of FIG. 1.

The proximal balloon 104 can carry the first part 100a, which can be a combination including a first frame structure 108, also called a stent, and a first valvular structure 202, also called a valve (FIG. 2A). The valvular structure 202 can be a "temporary" or "transient" valve, which can have a durability estimated to last between a few minutes and a few days. The valvular structure 202 can be made of any biocompatible synthetic material, such as polyester, polytetrafluoroethylene or polyurethane. Additionally, biocompatible synthetic materials that dissolve can be used. Alternatively, a natural tissue, such as pericardial tissue (e.g. bovine, porcine or equine pericardium), or other biological tissue, can be used. Proximal balloon 104 can be mounted within first frame structure 108 in its deflated state, prior to the introduction of first part 100a.

The first part 100a functions to stent open the native aortic valve using a strong first frame structure 108, which is provided to scaffold the dilated stenosed aortic valve. The size and shape of first frame structure 108 can be designed to ensure that it resists the recoil of the dilated valve so that it can be securely embedded in the remains of the native aortic valve. For example, the first frame structure 108 can be designed with stronger, thicker struts relative to that of the second part 100b, which can increase the diameter of the first frame in the crimped state. The first frame structure 108 can include a form of connectors, such as hooks or barbs, to help secure first frame structure 108 to the native aortic valve.

Once deployed, the valvular structure 202 of first part 100a can function hemodynamically as a replacement for the native heart valve leaflets until second part 100b can be deployed. Since valvular structure 202 can be a temporary valve, it does not need to be as durable as a typical valve prosthesis and, therefore, it can be made to occupy less space. For example, the valvular structure 202 can have relatively thin leaflets so that it has a reduced diameter in the crimped state.

First part 100a then provides a basis for anchoring second part 100b upon deployment of second part 100b. Beneficially, the deployment of first part 100a into the native aortic valve is provided with a sealing agent to prevent paravalvular leaks, which are leaks between first part 100a and the native valve.

Figure 2B:
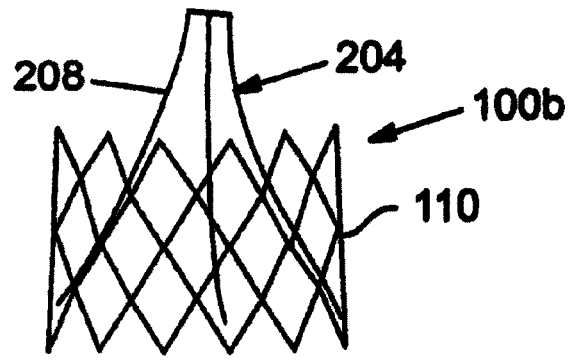

In one embodiment, the distal balloon 106 carries second part 100b, which includes a combination of a second frame structure 110 (or a second stent) and a "main" or "long-term" replacement valve 204 (FIG. 2B), which is a second valvular structure. The second valvular structure can be highly durable and exhibit excellent hemodynamic performance. The valve 204 can be made from biological matter, such as natural tissue, pericardial tissue (e.g., bovine, porcine or equine pericardium), a harvested natural valve, or other biological tissue. Alternatively, the valve can be made from biocompatible synthetic materials (e.g., biocompatible polymers), which are well known in the art. Distal balloon 106 does not need to be as strong as proximal balloon 104 and, therefore, can be made thinner, to occupy less space, making it easier to expand with lower pressure balloon inflation.

One difference between first part 100a and second part 100b is that second frame structure 110 does not need to be as strong as first frame structure 108, thus making it easier to expand with low balloon pressure inflation, which does not risk damaging the second valvular structure 204. Accordingly, second frame structure 110 can be sized and shaped with thinner struts than first frame structure 108. As a result, the second frame structure 110 can have a smaller diameter than the first frame structure 108, when both are in a crimped state. However, the comparatively larger crimped volume of the first frame structure 108 is offset, to some degree, by being associated with a thinner valvular structure 202. More particularly, valvular structure 202 can be thinner than valvular structure 204 and, therefore, has a smaller diameter than valvular structure 204, when both are in the crimped state. Thus, the overall diameter in the crimped state of each part 100a and 100b is reduced because a larger stent 108 is combined with a smaller valve 202 and a larger valve 204 is combined with a smaller stent 110.

Figure 6:
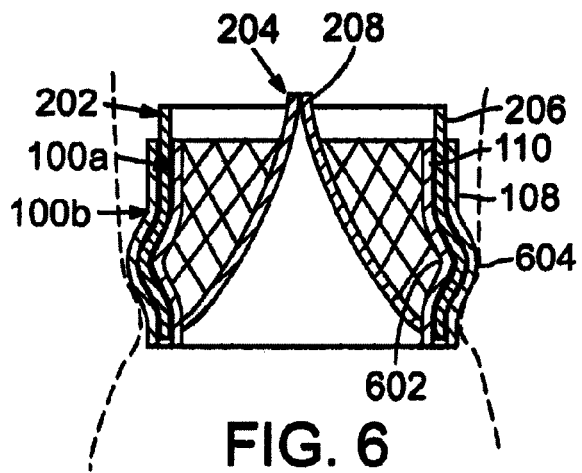
FIG. 6 is a cross-sectional view of an embodiment including geometrically mating stents.

Second part 100b is deployed such that it mounts to first part 100a. It should be understood that any type of fastening configuration or means can be used to attach second frame structure 110 to first frame structure 108. In one embodiment, the means of attachment between the two frames can be the use of friction. In this embodiment, the outer surface of second frame structure 110 can be made having a "rougher" surface to enhance the frictional relationship between the two frames. In another embodiment, hooks or barbs disposed on the surface of second frame structure 110 can be use to interlock into the cells created by the struts of first frame structure 108. In yet another embodiment of the attachment means can include the formation of a geometrical shape onto one or both of first and second frame structures 108 and 110 that provide a fixation in a mechanical male to female type connection. FIG. 6 described further below shows such a mechanical connection.

Figure 3E:
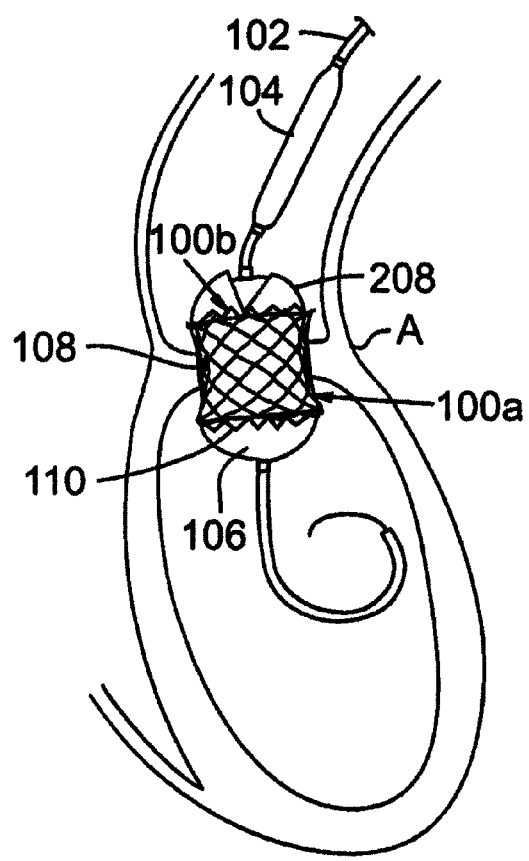

FIGS. 3A-3F are simplified illustrations showing a method of deploying the two-part implantable valve 100 in a cardiac valve (the aortic valve is used for illustrative purposes, but the method also applies to other cardiac valves). In FIG. 3A, catheter 102 is advanced through body lumens along guidewire 302 to the native aortic valve A until distal balloon 106 with second part 100b is disposed in the left ventricle and proximal balloon 104 with first part 100a is positioned in the aortic valve A.

As shown in FIG. 3B, proximal balloon 104 is inflated under relatively high pressure to expand first frame structure 108 of first part 100b. In one embodiment, first frame structure 108 can be expanded to a diameter greater than the aortic valve annulus, thereby compressing the native leaflets and/or stretching the aortic annulus during deployment. Such over expansion enhances the fixation of first frame structure 108 within the annulus. Over-expansion of first frame structure 108 also decreases residual gaps between the annulus and first part 100a, thereby reducing or eliminating undesirable leakage around the perimeter.

The expansion of proximal balloon 104 and the positioning of first part 100a are typically performed within a few seconds. In one embodiment, as shown in FIG. 3C, because during the balloon inflation the aortic orifice A is obstructed by proximal balloon 104 and the cardiac output is zero, proximal balloon 104 can be immediately deflated (e.g., within less than 5 or 6 seconds). Beneficially, as soon as the deflation has begun, the closing and opening states of leaflets 206 of valvular structure 202 (FIG. 2A) are allowed to function so that the valve becomes operational. Proximal balloon 104 can also be pulled back briskly in the aorta to allow leaflets 206 to function as soon as possible. Because the deployment of first part 100a is completed quickly, aortic regurgitation towards the left ventricle is reduced, thus reducing the possibility of inducing a massive pulmonary edema and a drop to zero of the cardiac output.

As shown in FIG. 3D, as proximal balloon 104 is withdrawn into the aorta, distal balloon 106 carrying second part 100b is moved into position within the aortic valve and within first frame structure 108 and leaflets 206. As shown in FIG. 3E, after second part 100b is properly positioned, distal balloon 106 is inflated to expand second part 100b. The inflation of distal balloon 106 causes second frame structure 110 to push and compress the first valvular structure 202 between the first frame structure 108 and the second frame structure 110.

Figure 3F:
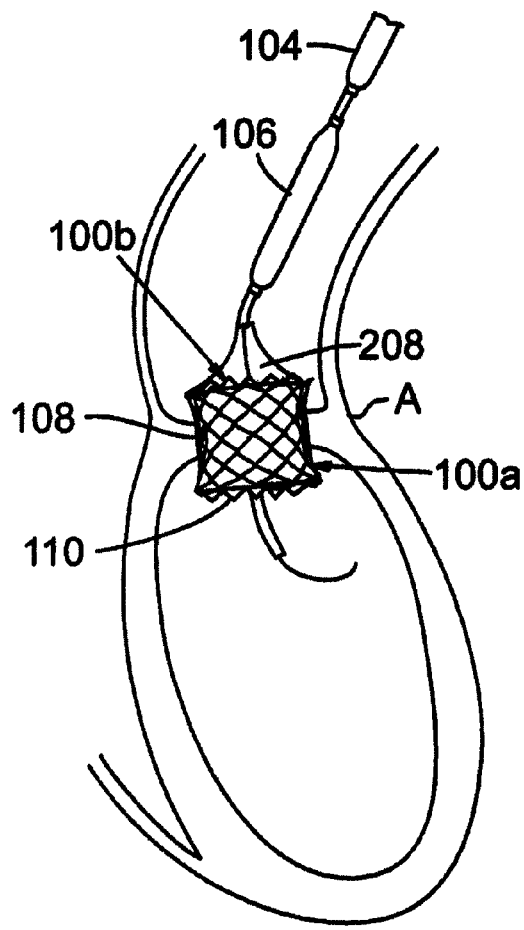

As shown in FIG. 3F, when second frame structure 110 is properly attached to first frame structure 108, distal balloon 106 is deflated and removed. Beneficially, as soon as the deflation has begun, the closing and opening states of leaflets 208 of valvular structure 204 (FIG. 2B) are allowed to function.

In an alternative embodiment, first frame structure 108 and/or second frame structure 110 can be self-expanding at the aortic valve. For example, first part 100a is expanded using proximal balloon 104, as generally shown in FIGS. 3A-3C. The second part 100b, having the main valve attached thereto, is advanced to a location within first frame structure 108 and is allowed to self-expand. Alternatively, both frame structures 108 and 110 can be self-expandable and deployed accordingly. Examples of self-expanding implantable valves and associated delivery methods suitable for use can be found in U.S. Application Publication No. 2004/0186563, filed Mar. 18, 2003, which is incorporated by reference herein in its entirety.

In another alternative embodiment, it will be appreciated that a double balloon catheter 102 is not necessary to deploy the two-part valve 100 and can be deployed using two separate catheters. For example, in one embodiment, first part 100a can be deployed using a first catheter. Subsequently, second part 100b can be deployed using a second catheter.

The two-part implantable valve 100 has been described for purposes of illustration, as being advanced percutaneously through the aorta in a retrograde direction for implantation at the site of a native aortic valve. However, a variety of alternative procedures can also be used. For example, the two-part implantable valve 100 can be advanced in an antegrade direction, such as by using a transseptal route. Furthermore, it will be appreciated that the general principles of the procedures shown in FIGS. 3A-3F can be applied in alternative minimally invasive approaches, such as, for example, by passing the prosthetic valve through a small incision in the chest wall (the transapical approach).

FIG. 6 shows a cross-sectional view of an example of the frames and valvular structures after deployment. In this particular embodiment, the first frame structure 108 can be made having a first geometrical feature 602, such as a detent. The second frame structure 110 can also include a second geometrical feature 604, such as an indentation, channel or groove that corresponds and mates with first geometrical feature 602. Upon deployment of second part 100b into first part 100a, first geometrical feature 602 is made to seat in second geometrical feature 604 to secure the frames together. In between the first frame structure 108 and the second frame structure 110, the temporary valve 202 can be compressed, which can also provide a good seal to reduce paravalvular leakage.

Figure 7:
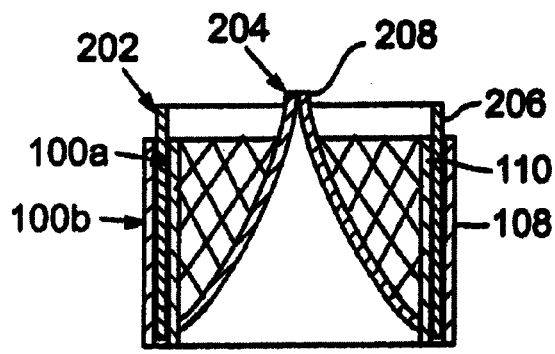
FIG. 7 is a cross-sectional view of an embodiment illustrating first and second stents with a temporary valve compressed therebetween

FIG. 7 shows another cross-sectional view, similar to FIG. 6, but without a geometrical feature for mating the two frame structures. The valvular structure 202, including the leaflets 206 are compressed between the first and second stents, 108, 110, to create a seal extending from a bottom to the top of the stent 110. The compressed valvular structure increases friction and reduces paravalvular leakage.

Advantageously, the two-part implantable valve 100 allows for a soft and mobile valvular structure 204 in second part 100b, which is capable of opening and closing freely in the blood stream without risk of being damaged by the balloon inflation. First part 100a provides a stent structure capable of withstanding a strong pressure inflation of the expanding balloon, without undue concern over the risks to valvular structure 202 due to its temporary nature.

The following relates to the determination method for matching a given stenotic heart valve and the appropriate percutaneous valve size (diameter).

A estimate of the adequate PHV size can be based on ultrasound measurement of the annulus, on angiographic images and on the physician's expertise. In this technique, before PHV implantation, a balloon valvuloplasty can be performed. The purpose of the balloon valvuloplasty is to prepare the implantation site and to make estimates for the proper PHV size.

Figure 4:
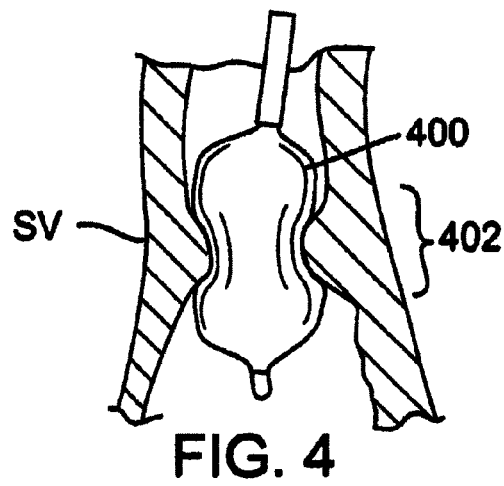
FIG. 4 is a simplified illustration of a balloon inflated inside a stenotic valve during balloon valvuloplasty procedure.

FIG. 4 is a simplified illustration of a balloon 400 inflated inside a stenotic valve SV during a balloon valvuloplasty procedure. As shown, balloon 400 can create a narrowed region 402 or "waist" when being inflated in the contact area with the diseased valve.

As previously mentioned, the axial retention force for securing the PHV to the native stenotic valve SV can be created by the radial contact forces applied by the stenotic valve SV on the outer surface of the PHV support frame. The minimal radial force that holds the PHV, divided by the surface area of a cylinder, representing the solid outer area of the PHV support frame, can provide the minimal pressure ($P_m$) to hold the PHV in position.

The basic assumption of the sizing method is that the minimal pressure ($P_m$) can be determined by in vitro and in vivo tests. Accordingly, it is assumed that the pressure $P_m$ is known quantity.

Figure 5:
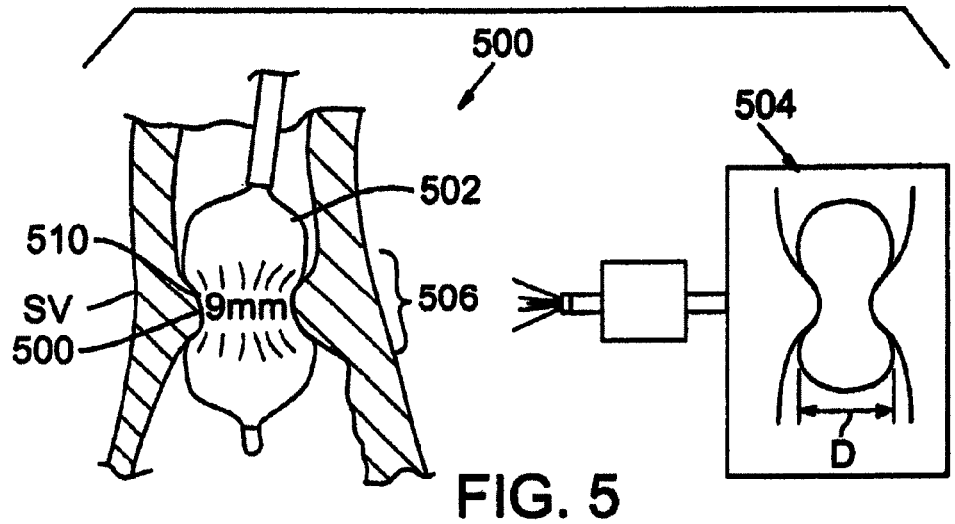
FIG. 5 is a simplified illustration of a tool for correlating the size of a heart valve to a native valve.

FIG. 5 is a simplified representation of a tool 500 for determining an adequate PHV size for a given stenotic valve SV. In one embodiment, a balloon 502 is inflated inside the stenotic valve SV to a pressure of $P_m$. When this pressure is reached, an angiographic image 504 can be taken and the balloon diameter D in the waist area 506 can be measured. Diameter D represents the minimum PHV diameter to be implanted.

At pressure $P_m$, balloon 502 can develop a waist 506 to ensure that balloon wall 510 at waist area 506 is not loaded and that the total pressure $P_t$ at waist area 506 can be applied on the native stenotic valve SV.

In one embodiment, for ease of implementation, a table can be created and made available for the physician that correlates between diameter D of waist area 506 and the adequate PHV size. The measuring procedure described above can be performed: 1) as a part of a balloon valvuloplasty procedure performed prior to a PHV implantation; or 2) after the balloon valvuloplasty procedure.

Balloon 502 can be a compliant balloon or a noncompliant balloon. If a non compliant balloon is used, then its inflated diameter can be larger than waist diameter D in order to ensure balloon wall 510 is not resisting the pressure at waist area 506 and that total pressure $P_t$ is held by the native stenotic valve SV.

If a compliant balloon is used, the curve of pressure vs. diameter of balloon 502 should be known and the pressure that the native valve SV actually resists can be calculated accordingly.

Balloon 502 can be inflated by a liquid that contains a contrast die so that the shape of balloon 502 is visible under fluoroscopy.

FIG. 8 shows a flowchart 800 of a method for implanting the two-stent structure. In process block 802, a temporary valve and stent are advanced into the patient, such as using one or more delivery catheters in a transvascular or transapical approach. In process block 804, the temporary valve and stent are positioned in the native valve. The stent and valve are then expanded (process block 806) into the native valve. Such expansion can be effected through a balloon or the stents can be self expanding. In any event, the temporary valve becomes operational so that the patient has cardiac output. In process block 808, a replacement valve and a second stent are advanced into the patient. The second stent and the replacement valve are positioned within the temporary valve. For example, the first and second stent can have their top and bottom edges aligned or corresponding geometrical configurations can be aligned. Once the second stent is aligned, in process block 812, the second stent is expanded either using a balloon or through self expansion. In any event, the second stent compresses the temporary valve against the first stent so that the temporary valve is sandwiched there betweenIn view of the many possible embodiments to which the principles of the disclosed invention can be applied, it should be recognized that the illustrated embodiments are only preferred examples of the invention and should not be taken as limiting the scope of the invention. Rather, the scope of the invention is defined by the following claims. We therefore claim as our invention all that comes within the scope of these claims.

We claim:

1. A method of treating a defective native aortic valve in a human heart, comprising:
   creating an incision in a chest wall of a patient and accessing the native aortic valve through an apex of the heart;
   advancing a balloon through the incision in the chest wall and inflating the balloon within the native aortic valve;
   advancing a first percutaneously implantable heart valve in a crimped state through the incision in the chest wall and apex of the heart, the first percutaneously implantable heart valve comprising a radially-expandable first stent supporting a radially-expandable temporary valve within an interior portion of the first stent;
   positioning the first stent within the native aortic valve;
   expanding the first stent to an operational diameter within the native aortic valve, compressing the native leaflets, so that the temporary valve becomes operational;
   while the incision in the chest wall remains open, advancing a second percutaneously implantable heart valve in a crimped state through the incision in the chest wall and apex of the heart, the second percutaneously implantable heart valve comprising a radially-expandable second stent supporting a radially-expandable replacement valve within an interior portion of the second stent;
   positioning the radially-expandable second stent within the operational temporary valve of the expanded first stent; and
   expanding the radially-expandable second stent so as to compress the temporary valve between the first stent and the second stent while maintaining the first stent at the operational diameter;
   wherein, after expansion of the second stent, the replacement valve becomes operational for replacing the function of the defective native aortic valve.

2. The method of claim 1, wherein the second stent has a top end and a bottom end and the temporary valve, in its compressed state between the first and second stents, extends either from the top end to the bottom end of the second stent or extends within the top end to the bottom end of the second stent so as to minimize paravalvular leakage.

3. The method of claim 1, wherein expanding the first stent includes inflating a first balloon on a delivery catheter and expanding the second stent includes inflating a second balloon on the delivery catheter, the second balloon being spaced apart from the first balloon on the delivery catheter.

4. The method of claim 3, wherein inflating the first balloon and inflating the second balloon comprises inflating the first balloon at a pressure greater than the second balloon.

5. The method of claim 1, wherein the temporary valve is made of a biocompatible synthetic material, including one or more of the following:
   a) polyester, polytetrafluoroethylene, or polyurethane; or
   b) biocompatible synthetic material that dissolves; or
   c) natural tissue, including pericardial tissue or other biological tissue.

6. The method of claim 1, further including determining a size of the replacement valve by inflating a test balloon inside the cardiac valve to a desired pressure and taking an angiographic image of the test balloon to determine a diameter of the test balloon.

7. The method of claim 1, wherein the temporary valve, in its compressed state between the first and second stents, serves as a friction barrier.

8. The method of claim 1, wherein the temporary valve is thinner than the replacement valve so as to minimize a crimp profile of the temporary valve.

9. The method of claim 1, wherein the first stent has a larger crimp profile than the second stent and the temporary valve has a smaller crimp profile than the replacement valve.

10. The method of claim 1, wherein expanding the first stent comprises over expanding the first stent.

11. The method of claim 1, wherein positioning the radially-expandable second stent within the operational temporary valve of the first stent comprises mating a first geometrical feature of the first stent with a complementary second geometrical feature of the second stent.

12. The method of claim 1, advancing the first percutaneously implantable heart valve comprises advancing a first percutaneously implantable heart valve comprising a temporary valve comprising leaflets with an operational life of from a few minutes to a few days.

13. A method of implanting a prosthetic cardiac valve within a native heart valve, comprising:
   deploying a temporary valve and expanding a radially-expandable first stent in the native heart valve so that the first stent has a first diameter in which the temporary valve is operational; and
   during the same implantation procedure deploying a replacement valve and a second stent by inserting the replacement valve and the second stent into the operational temporary valve and by expanding the replacement valve and second stent so as to compress the temporary valve between the first and second stents, while maintaining the first stent at the first diameter;
   wherein the first and second stents are advanced using a common delivery catheter having first and second balloons coupled in series.

14. The method of claim 13, wherein deploying the temporary valve and the first stent includes inflating a first balloon to a first pressure and expanding the replacement valve and the second stent includes inflating a second balloon to a second pressure, which is less than the first pressure.

15. The method of claim 13, wherein the second stent has a top end and a bottom end and the temporary valve, in its compressed state, extends either from the top end to the bottom end of the second stent or extends within the top end and the bottom end of the second stent so as to prevent paravalvular leakage.

16. The method of claim 13, wherein the first and second stents have mating geometrical configurations to assist with proper positioning of the first and second stents.

17. The method of claim 13, wherein the temporary valve is made of biocompatible synthetic material, including one of the following:
   polyester, polytetrafluoroethylene, or a polyurethane.

18. The method of claim 13, wherein the temporary valve is made of a synthetic or biocompatible material that dissolves over time.

19. The method of claim 13, wherein the temporary valve is made of natural tissue, pericardial tissue, bovine pericardium, porcine pericardium, equine pericardium or other biological tissue.

20. The method of claim 13, wherein the first stent has a larger crimp profile than the second stent and the temporary valve has a smaller crimp profile than the replacement valve.

21. The method of claim 13, wherein deploying a temporary valve and a first stent in the native heart valve comprises over expanding the first stent.

22. The method of claim 13, wherein the first stent comprises stronger struts than the second stent.

* * * * *